United States Patent [19]

Avar et al.

[11] 4,165,267

[45] Aug. 21, 1979

[54] PHOTO-POLYMERIZABLE SYSTEMS CONTAINING 2-HALOACETOPHENONE DERIVATIVES AS PHOTOSENSITIZING AGENTS

[75] Inventors: Lajos Avar, Binningen; Kurt Hofer, Munchenstein, both of Switzerland

[73] Assignee: Sandoz Ltd., Basel, Switzerland

[21] Appl. No.: 884,006

[22] Filed: Mar. 6, 1973

Related U.S. Application Data

[63] Continuation of Ser. No. 781,309, Mar. 25, 1977, abandoned, which is a continuation of Ser. No. 612,502, Sep. 11, 1975, abandoned.

[30] Foreign Application Priority Data

Sep. 19, 1974 [CH] Switzerland ..................... 12728/74

[51] Int. Cl.$^2$ .............................. C08F 8/18; C08F 8/34
[52] U.S. Cl. ............................. 204/159.15; 96/115 P; 204/159.16; 204/159.18; 204/159.19; 204/159.23; 204/159.24; 260/23 EP; 427/54; 428/413; 428/481; 428/514
[58] Field of Search ................. 96/115 P; 204/159.18, 204/159.23, 159.24, 159.15, 159.16, 159.19

[56] References Cited

U.S. PATENT DOCUMENTS

| | | |
|---|---|---|
| 3,759,807 | 9/1973 | Osborn et al. ................... 204/159.23 |
| 3,850,989 | 11/1974 | Havinga et al. ..................... 260/592 |
| 3,929,490 | 12/1975 | Reiter et al. ....................... 96/115 P |

*Primary Examiner*—Richard B. Turer
*Attorney, Agent, or Firm*—Gerald D. Sharkin; Richard E. Vila; Thomas C. Doyle

[57] ABSTRACT

The present invention concerns novel photopolymerizable formulations which comprise a photopolymerizable system in association with a photosensitizing amount of the compound of formula

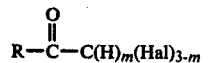

wherein
R is an unsubstituted or substituted binuclear aromatic group, e.g. phenoxy phenyl,
m is 0, 1 or 2 and
Hal is halogen.

15 Claims, No Drawings

PHOTO-POLYMERIZABLE SYSTEMS CONTAINING 2-HALOACETOPHENONE DERIVATIVES AS PHOTOSENSITIZING AGENTS

This is a continuation of application Ser. No. 781,309, filed Mar. 25, 1977, which in turn is a continuation of application Ser. No. 612,502, filed Sept. 11, 1975 both of which prior applications are now abandoned.

The present invention relates to photo-polymerisable formulations and more specifically to such formulations which include a photo-sensitizing agent to initiate and accelerate polymerisation on exposure to light.

Accordingly, the present invention provides a photo-polymerisable formulation which comprises a photo-polymerisable system in association with a photo-sensitizing amount of a compound of formula I, $$R-\overset{O}{\underset{\|}{C}}-C(H)_m(Hal)_{3-m} \qquad I$$

wherein R is an unsubstituted or substituted radical of formula a

wherein $X_1$ is a direct covalent bond or is —O—, —S—, —SO—, —SO$_2$—
or

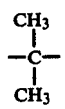

and either $X_2$ and $X_3$ are each hydrogen or, when $X_1$ is a direct covalent bond, $X_2$ and $X_3$ together may also form one of the bridge members —O—, —S—, —SO— or —SO$_2$—,
Hal is chlorine or bromine,
and m is 0, 1 or 2, any substituents on the radical of formula a being selected such that the U.V. absorption maximum of the resulting compound of formula I lies in the range 250–400 nm, especially 270–360 nm.

As will be appreciated, the selection of substituents on the radical of formula a forms part of the general knowledge in the photo-sensitizer art.

Preferably, the formulation includes as photo-sensitizing agent a compound of formula Ia $$R'-\overset{O}{\underset{\|}{C}}-C(H)_m(hal)_{3-m} \qquad Ia$$

wherein Hal and m are as defined above and R' is a radical of formula aa

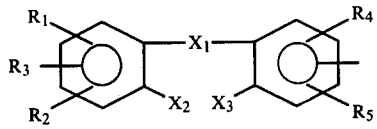

wherein $X_1$, $X_2$ and $X_3$ are as defined above,
each of $R_1$, $R_2$, $R_4$ and $R_5$ is, independently, hydrogen or alkyl($C_1$–$C_{18}$) with up to $C_{18}$ in the aggregate of all of the substituents $R_1$, $R_2$, $R_4$ and $R_5$
and $R_3$ is hydrogen, halogen or a radical $$R_6-\overset{O}{\underset{\|}{C}}-$$

wherein $R_6$ is —C(H)$_m$(Hal)$_{3-m}$
wherein Hal and m are as defined above, furenyl, thienyl, phenyl or phenyl substituted by 1 alkyl(-$C_1$–$C_4$) or 1 or 2 halogen substituents.

More preferably, the formulation includes as photo-sensitizing agent a compound of formula Ib $$R''-\overset{O}{\underset{\|}{C}}-C(H)_m(Hal)_{3-m} \qquad Ib$$

wherein Hal and m are as defined above and R'' is a radical of formula ab

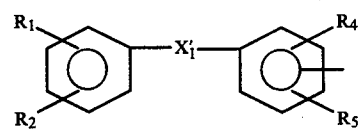

wherein $R_1$, $R_2$, $R_4$ and $R_5$ are as defined above, and $X_1'$ is —O— or —S—,
more preferably a radical of formula ab'

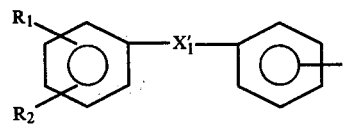

wherein $R_1$, $R_2$ and $X_1'$ are as defined above.

In particular, the formulation preferably includes as photo-sensitizing agent a compound of formula Ic

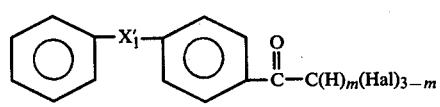

wherein $X_1'$, Hal and m are as defined above.

By the term halogen is meant chlorine, bromine or iodine, preferably chlorine or bromine, particularly chlorine.

When any of $R_1$, $R_2$, $R_4$ and $R_5$ are alkyl, this is preferably $C_1$–$C_{12}$, more preferably $C_1$–$C_8$, especially $C_1$–$C_6$, and in particular $C_1$–$C_4$, e.g. methyl. Such alkyls may be straight or branched chain, primary, secondary or tertiary. Of course, when both $R_1$ and $R_2$ and/or both $R_4$ and $R_5$ are tertiary alkyl, they are normally not on adjacent carbon atoms.

Preferably R$_4$ and R$_5$ are each hydrogen.
When R$_3$ is a group

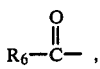

then R$_6$ is preferably —C(H)$_m$(Hal)$_{3-m}$.
Preferably R$_3$ is hydrogen or

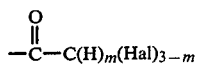

especially hydrogen.

Preferably R$_3$, when a substituent, occupies a para position in relation to X$_1$ or, when X$_2$ forms part of a bridge member, to X$_2$.

Preferably the free bond of the radical a occupies a para position in relation to X$_1$ or, when X$_3$ forms part of a bridge member, to X$_3$.

Preferably the radical a is based on one of the following ring structures, viz.

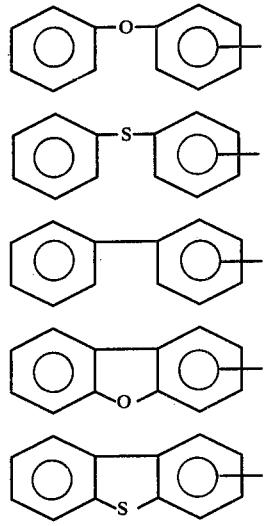

particularly ac, ad, ae and af, especially ac and ad.

The compounds of formula I are generally known. Insofar as they are not known, they may be produced in analogous manner to the processes for producing the known compounds, e.g. by the Friedel-Crafts reaction.

The present invention also provides a method of photo-polymerising a photo-polymerisable system which comprises irradiating said system with U.V. light of wave length 250-400 nm in the presence of a photo-sensitizing amount of a compound of formula I.

It is to be understood that the terms "photo-polymerising" and "photo-polymerisable" are employed herein in a broad sense to include e.g. cross-linking of polymeric materials, such materials being referred to herein as "prepolymers", as well as simple homo- co- and ter-polymerisation of monomers.

Any of the conventional light sources providing light of wave length 250-400 nm may be employed, such as sunlight or actinic light from e.g. a sun ray lamp or mercury arc lamp.

Photo-polymerisable systems suitable for use in the formulations of the present invention are in general known, e.g. in the U.V. curable coating and printing ink arts. Such systems are preferably those capable of polymerising by a free radical mechanism and in general the polymerising species is/are unsaturated. The systems may be mono- or multi-component. It is preferred that the system contain at least one multi-functional component to promote photo-initiated cross-linking. In addition, it is preferred that at least one component of the system is, or is derived from, an unsaturated carboxylic acid, in particular an α,β-unsaturated carboxylic acid such as acrylic or methacrylic acid.

Preferably the system is multi-component and more preferably comprises one or more reactive base prepolymers or long chain monomers in association with one or more cross-linking monomers. Preferred reactive base prepolymers are unsaturated polyethers, polyesters, polyester-based urethanes or epoxy resins or saturated or unsaturated such polymers modified by esterification with an unsaturated carboxylic acid. Preferred examples of reactive base prepolymers are acrylated or methacrylated hydroxy-functional polyethers, polyesters, polyester-based-urethanes or epoxy resins or unsaturated polyesters. Examples of reactive base long chain monomers are acryl derivatives of epoxylated unsaturated fatty acids, e.g. acryl derivatives of epoxylated linseed oil. Examples of cross-linking monomers are vinyl and allyl monomers, e.g. styrene, trimethylol propane diallyl ether and vinyl and allyl esters such as vinyl acrylate and diallyl maleate and phthalate, acrylated alcohols, e.g. acrylated phenoxyethyl alcohol, and multi-functional acrylates such as acrylated polyols, e.g. acrylated neopentyl glycol and pentaerythritol.

The photo-polymerisable formulations of the present invention are of particular interest as U.V. curable coatings, e.g. coating lacquers, and printing inks, e.g. offset lithographic printing inks.

For such use, the formulations are preferably of resinous form and contain no or minimal (i.e. less than 1%) non-reactive solvent. In the case of multi-component systems comprising a reactive base prepolymer or long chain monomer and at least one cross-linking monomer, the cross-linking monomer is preferably selected inter alia in accordance with the solvent properties thereof to provide the desired viscosity characteristics for the final formulations.

Other agents, e.g. anti-oxidants, pigments and fillers, may also be employed in the above-mentioned formulations.

The exact composition of such formulations is not critical and may be varied to suit the intended use.

The amount of photo-sensitizing agent employed in the photo-polymerisable formulations of the invention will vary depending on the proposed use. However, in general, satisfactory results may be obtained when employed in an amount of from 0.01 to 10%, preferably 0.05 to 5%, of the weight of the polymerisable system.

The invention is illustrated by the following Examples wherein parts and percentage are by weight and temperatures are in °Centigrade.

EXAMPLE 1

A photo-polymerisable system consisting of 60 g of a prepolymer of the formula

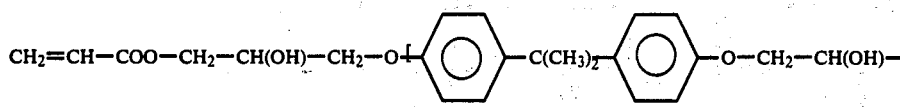

having a viscosity of about 9000 poise at 77° C. (cf. U.S. Pat. No. 3,713,864), and 35 g pentaerithritol tetraacrylate and 5 g of a photo-sensitizer of the formula

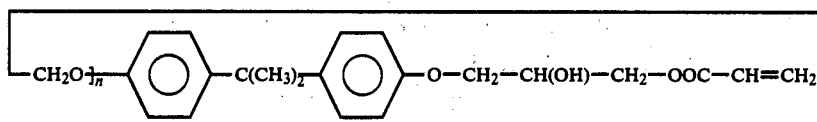

were applied with a spatula in an amount of 3.5 g/m² to matt art paper and cured in a U.V. Mini-Cure at a belt speed of 71.6 m/min. to give a non-sticky, shiny film.

In analogous manner, the photo-sensitizers set out in the following Tables 1 and 2 are employed.

TABLE 1

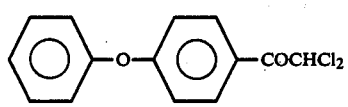

| Ex. No. | $R_1$ | $R_2$ | m |
|---|---|---|---|
| 2 | H | H | 0 |
| 3 | " | " | 1 |
| 4 | " | " | 2 |
| 5 | n-C$_4$H$_9$ | " | 0 |
| 6 | " | " | 1 |
| 7 | CH$_3$ | CH$_3$ | 0 |
| 8 | " | " | 1 |
| 9 | " | " | 2 |
| 10 | n-C$_{12}$H$_{25}$ | " | 0 |
| 11 | " | " | 1 |
| 12 | " | " | 2 |

TABLE 1-continued $R_1$—⌬(—O—⌬—C(=O)—C(H)$_m$(Cl)$_{3-m}$) with $R_2$ substituent

| Ex. No. | $R_1$ | $R_2$ | m |
|---|---|---|---|
| 13 | —C(=O)—C(H)$_m$(Cl)$_{3-m}$ | H | 0 |
| 14 | " | " | 1 |
| 15 | " | " | 2 |
| 16 | Cl | " | 1 |
| 17 | (furan-2-yl-C(=O)—) | " | 1 |
| 18 | (2-Cl-phenyl-C(=O)—) | " | 1 |
| 19 | (4-(CH$_3$)$_3$C-phenyl-C(=O)—) | " | 1 |
| 20 | (phenyl-C(=O)—) | " | 1 |
| 21 | I | " | 0 |
| 22 | " | " | 1 |

TABLE 2

| Ex. No. | Formula | Ex. No. | Formula |
|---|---|---|---|
| 23 | phenyl-O-phenyl-C(=O)-CHBr$_2$ | 31 | dibenzofuran-C(=O)-CH$_2$Cl |
| 24 | phenyl-O-phenyl-C(=O)-CBr$_3$ | 32 | dibenzofuran-C(=O)-CHCl$_2$ |
| 25 | biphenyl-C(=O)-CH$_2$Cl | 33 | dibenzofuran-C(=O)-CCl$_3$ |
| 26 | biphenyl-C(=O)-CHCl$_2$ | 34 | dibenzothiophene-C(=O)-CH$_2$Cl |

TABLE 2-continued

| Ex. No. | Formula | Ex. No. | Formula |
|---|---|---|---|
| 27 | Ph-Ph-C(=O)-CCl₃ | 35 | Ph-C(CH₃)₂-Ph-C(=O)-CHCl₂ |
| 28 | Ph-S-Ph-C(=O)-CH₂Cl | 36 | Cl₂HC-C(=O)-Ph-C(CH₃)₂-Ph-C(=O)-CHCl₂ |
| 29 | Ph-S-Ph-C(=O)-CHCl₂ | 37 | Cl₂HC-C(=O)-Ph-SO₂-Ph-C(=O)-CHCl₂ |
| 30 | Ph-S-Ph-C(=O)-CHBr₂ | 38 | ClH₂C-C(=O)-Ph-S-Ph-C(=O)-CH₂Cl |
|  |  | 39 | Cl₂HC-C(=O)-Ph-S-Ph-C(=O)-CHCl₂ |
|  |  | 40 | Br₂HC-C(=O)-Ph-Ph-C(=O)-CHBr₂ |

EXAMPLE 41

A photo-polymerisable system consisting of 50 parts of the acryl derivative of epoxylated linseed oil (2.9 acryl groups per molecule on average), 20 parts of neopentyl glycol diacrylate and 27 parts of phenoxyethyl acrylate, and 5 parts of a photo-sensitizer of the formula

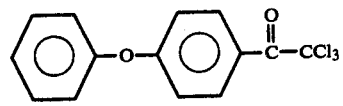

were applied onto matt art paper and cured in the manner described in Example 1.

EXAMPLE 42

100 Parts of a photo-polymerisable system consisting of 67 parts of polyester (produced from maleic acid anhydride, phthalic acid anhydride and propan-1,2-diol) and 33 parts styrene, and 3 parts of a photo-sensitizer of the formula

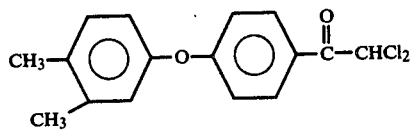

as well as 0.1 parts by weight of paraffin oil, were applied and cured in accordance with the procedure of Example 1.

The Example is repeated employing the photo-sensitizers of the formulae

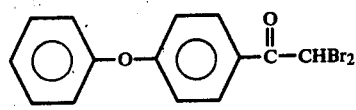

and

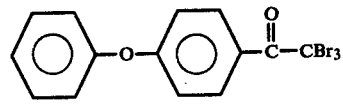

EXAMPLE 43

A polymerisable polyester based acrylated urethane system is produced by reacting an hydroxy functional saturated polyester (produced from adipic acid, ethylene glycol and 1,6-hexane-diol) with the reaction product of toluene di-isocyanate and β-hydroxyethyl acrylate. 70 Parts of the resulting system is employed in association with 30 parts of pentaerythritol triacrylate and 3 parts of the photo-sensitizer of the formula

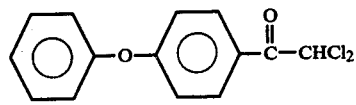

in analogous manner to that described in Example 1.

The Example is repeated employing an unsaturated polyester produced from maleic acid anhydride, diethylene glycol and 1,3-butylene glycol.

In analogous manner to the procedures described in Examples 41 to 43, the photo-sensitizers of Examples 2 to 40 may be employed.

The compounds employed in the preceding Examples may be produced according to or in analogous manner to the procedure described in Examples A and B below.

EXAMPLE A 17.0 g Diphenyl ether and 11.3 g chloroacetyl chloride were dissolved in 200 ml of chlorobenzene. To the solution so formed at room temperature and with stirring were added 30 g of aluminium chloride over a period of 2 hours. The reaction mixture was stirred for a further 4 hours at 50°. After cooling, 100 ml of concentrated HCl and 200 ml of ice water were added thereto. The organic phase was separated off, washed with water, and the solvent distilled off. After further washing the compound of Example 4 of Table 1 is obtained. M.P. 55°–56°.

EXAMPLE B 16.9 g of 4-Trichloroacetyl-diphenyl ether were dissolved at 78° in a mixture consisting of 70 ml of acetic acid and 7 ml of water. To the solution so formed, still at 78°, were added successively 1.4 ml concentrated $H_2SO_4$, 2.1 g $HIO_3$ and 5.7 g Iodine. The reaction was allowed to proceed for 3 hours at 78° to 80°. The light brown reaction mixture was added to 400 ml of water whereby a yellowish oil separated out. The separated oil was taken up in 100 ml of toluene and separated from the aqueous phase. The toluene phase was washed neutral, the solvent distilled off, and the residue recrystallized from isopropanol. The compound of Example 21 of Table 1 was obtained in white crystalline form. M.P. 101°–103°.

In analogous manner the compound of Example 22 of Table 1 is obtained. M.P. 69°–72°.

We claim:

1. A photo-polymerizable composition which comprises (a) a photo-polymerizable system comprising at least one reactive unsaturated base prepolymer or long chain monomer in association with at least one unsaturated crosslinking monomer and (b) a photo-sensitizing amount of a compound of the formula

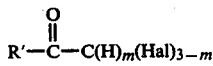

wherein R' is a radical of the formula

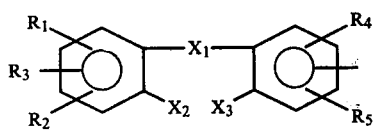

wherein $X_1$ is a direct covalent bond or is —O—, —S—, —SO—, —SO$_2$— or

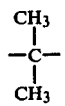

and either
$X_2$ and $X_3$ are each hydrogen or, when $X_1$ is a direct covalent bond, $X_2$ and $X_3$ together may also form one of the bridge members —O—, —S—, —SO— or —SO$_2$—, $R_1$, $R_2$, $R_4$ and $R_5$ are, independently, hydrogen or alkyl ($C_1$–$C_{18}$) with up to 18 carbon atoms in the aggregate of all of the substituents $R_1$, $R_2$, $R_4$ and $R_5$ $R_3$ is hydrogen, halogen or a radical

wherein
$R_6$ is —C(H)$_m$(Hal)$_{3-m}$, furenyl, thienyl, phenyl or phenyl substituted by 1 alkyl ($C_1$–$C_4$) or 1 or 2 halogen substituents, Hal is chlorine or bromine, and m is 0, 1 or 2,
any substituents on the radical of formula aa being such that the U.V. absorption maximum of the resulting compound lies in the range 250–400 nm.

2. A composition according to claim 1 wherein at least one of the components of the polymerisable system is multi-functional.

3. A composition according to claim 1 wherein at least one of the components of the system comprises or is derived from an unsaturated carboxylic acid.

4. A composition according to claim 1 in the form of a U.V. curable coating or printing ink resin, free or substantially free of non-reactive solvent.

5. A composition according to claim 1 wherein the photo-polymerizable system is capable of polymerizing by a free radical mechanism.

6. A composition according to claim 1 wherein the reactive base prepolymer is unsaturated and is selected from the group consisting of polyethers, polyesters, polyester-based urethanes and epoxy resins or is selected from said group and is saturated or unsaturated and modified by esterification with an unsaturated carboxylic acid, the reactive base long chain monomer is an acryl derivative of an epoxylated unsaturated fatty acid and the crosslinking monomer is selected from the group consisting of vinyl and allyl monomers, acrylated alcohols and acrylated polyols.

7. A composition according to claim 1 wherein at least one component of the photo-polymerizable system is or is derived from an α,β,-unsaturated carboxylic acid.

8. A method of producing a polymer which comprises irradiating with U.V. light of wave length 250 to 400 nm. a composition in accordance with claim 1.

9. A composition according to claim 1 wherein the photosensitizing compound is of the formula

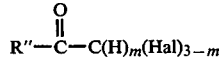

wherein R" is a radical of the formula

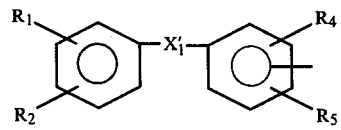

wherein $X_1'$ is —O— or —S— and Hal, $R_1$, $R_2$, $R_4$, $R_5$ and m are as defined in claim 1.

10. A composition according to claim 9 wherein the photosensitizing compound is of the formula

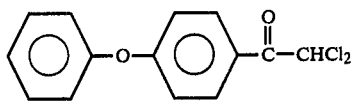

11. A polymer whenever produced by the process of claim 8.

12. A composition according to claim 1 wherein the photo-sensitizing compound is present in an amount of from 0.01 to 10% based on the weight of the photopolymerizable system.

13. A composition according to claim 12 wherein the photosensitizing compound is present in an amount of from 0.05 to 5% based on the weight of the photopolymerizable system.

14. A composition according to claim 10 wherein the photo-sensitizing compound is present in an amount of from 0.01 to 10% based on the weight of the photopolymerizable system.

15. A composition according to claim 14 wherein the photosensitizing compound is present in an amount of from 0.05 to 5% based on the weight of the photopolymerizable system.

* * * * *

UNITED STATES PATENT AND TRADEMARK OFFICE
CERTIFICATE OF CORRECTION

PATENT NO. : 4,165,267
DATED : August 21, 1979
INVENTOR(S) : Lajos Avar/Kurt Hofer It is certified that error appears in the above—identified patent and that said Letters Patent is hereby corrected as shown below:

On the front page; in the left-hand column;

"March 6, 1973" should read --March 6, 1978--.

Signed and Sealed this

Ninth Day of September 1980

[SEAL]

Attest:

SIDNEY A. DIAMOND

Attesting Officer

Commissioner of Patents and Trademarks